(12) United States Patent  
Hennig et al.

(10) Patent No.: US 8,831,736 B2
(45) Date of Patent: Sep. 9, 2014

(54) ELECTRIC THERAPY SYSTEM AND THERAPY DEVICE

(75) Inventors: Carsten Hennig, Berlin (DE); Joachim Elsner, Berlin (DE); Bernhard Gromotka, Berlin (DE)

(73) Assignee: Biotronik CRM Patent AG (CH)

( * ) Notice: Subject to any disclaimer, the term of this patent is extended or adjusted under 35 U.S.C. 154(b) by 697 days.

(21) Appl. No.: 12/563,263

(22) Filed: Sep. 21, 2009

(65) Prior Publication Data

US 2010/0076522 A1 Mar. 25, 2010

(30) Foreign Application Priority Data

Sep. 25, 2008 (DE) .......................... 10 2008 042 355

(51) Int. Cl.
*A61N 1/00* (2006.01)
*H04L 29/08* (2006.01)
*A61N 1/372* (2006.01)
*H04L 29/06* (2006.01)

(52) U.S. Cl.
CPC .......... *A61N 1/37252* (2013.01); *A61N 1/37217* (2013.01); *H04L 69/18* (2013.01); *H04L 67/12* (2013.01)
USPC ............................................... 607/60; 607/32

(58) Field of Classification Search
CPC ........... A61N 1/37252; A61N 1/37217; A61N 1/37223; A62B 2560/0219; H04L 67/12; H04L 69/18
USPC .................... 607/30–32, 59–60; 128/903–904
See application file for complete search history.

(56) References Cited

U.S. PATENT DOCUMENTS

| | | | |
|---|---|---|---|
| 6,400,990 B1* | 6/2002 | Silvian | 607/60 |
| 6,443,891 B1* | 9/2002 | Grevious | 600/302 |
| 8,108,048 B2* | 1/2012 | Masoud | 607/60 |
| 8,112,151 B1* | 2/2012 | Cogan et al. | 607/32 |
| 2004/0038645 A1 | 2/2004 | Reunamaki et al. | |
| 2005/0049656 A1* | 3/2005 | Petersen et al. | 607/60 |
| 2005/0113886 A1 | 5/2005 | Fischell et al. | |
| 2006/0030904 A1* | 2/2006 | Quiles | 607/60 |
| 2006/0116744 A1* | 6/2006 | Von Arx et al. | 607/60 |
| 2007/0060978 A1* | 3/2007 | Haubrich et al. | 607/60 |
| 2007/0116033 A1 | 5/2007 | Reunamaki et al. | |
| 2007/0167996 A1* | 7/2007 | Dudding et al. | 607/60 |
| 2008/0097912 A1 | 4/2008 | Dicks et al. | |
| 2010/0274323 A1* | 10/2010 | Williamson et al. | 607/60 |
| 2012/0065697 A1* | 3/2012 | Bange et al. | 607/32 |

FOREIGN PATENT DOCUMENTS

DE 603 05 108 T2 9/2006
WO WO 0224064 A1 3/2002

* cited by examiner

*Primary Examiner* — Catherine Voorhees
(74) *Attorney, Agent, or Firm* — Craig A. Fieschko, Esq.; DeWitt Ross & Stevens S.C.

(57) ABSTRACT

The invention relates to a therapy system and a therapy device having at least one data communication interface which can operate in various data transmission modes and cooperates with a data communication control unit. The data communication interface can change from one data transmission mode to another without interruption of an existing data link. The change is controlled by the data communication control unit as a function of predefined selection criteria.

22 Claims, 6 Drawing Sheets

ELECTRIC THERAPY SYSTEM AND THERAPY DEVICE

FIELD OF THE INVENTION

The invention relates to an electric therapy system having a therapy device, e.g., an implant, and an external device, e.g., a programming device. The therapy device and the external device each have a data communication interface designed for implementing bidirectional wireless data transmission to the other device. The data communication interfaces each contain or are connected to a data communication control unit.

BACKGROUND OF THE INVENTION

Electric therapy systems including therapy devices and external devices are known in the art. The therapy device of such a system may be an implant, for example, such as an implantable heart pacemaker, cardioverter/defibrillator or the like. The external device may be a programming device for such a therapy device, or a so-called patient device that serves as a relay station between the implant and a central service center.

The data communication interface of the therapy device (the therapy device data communication interface) and the data communication interface of the external device (the external device data communication interface) each have a transmitter and a receiver (together also known as a transceiver) to allow bidirectional data communication.

In the case of implantable heart pacemakers or cardioverters/defibrillators, the therapy device, e.g., the implant, often has two data communication interfaces. One of these therapy device data communication interfaces will often use an alternating magnetic field for wireless data communication. This data communication is usually used between a programming device and the implant and has only a very short range. This data communication is used, for example, when a patient who has a heart pacemaker is visiting his treating physician. The physician may then place a corresponding programming head of the programming device against the patient's body, thereby enabling short-range data communication between the implant and the programming head via an alternating magnetic field.

A second therapy device data communication interface is often provided for a somewhat longer-range data communication with an external device. This external device may be either a programming device or a patient device, which often serves as a relay station for data communication between an implant and a remote service center. Data communication may take place here via an alternating electric field in the so-called MICS band. The MICS band is a special frequency band for data communication between implants and external devices.

In any case, the at least one therapy device data communication interface of the implant must be supplied with power by a power source provided internally within the implant, which is typically a battery that inherently has only a limited capacity. If the battery of an implant, e.g., an implantable heart pacemaker, is depleted, the heart pacemaker must be explanted in a surgical procedure and replaced by a new one. There is therefore a need to minimize the power consumption by the therapy device. This requirement also applies to the power consumption for the bidirectional data link.

SUMMARY OF THE INVENTION

An object of the invention is to provide a therapy system and a therapy device which will allow an energy-saving and reliable data communication. This object can be achieved by an electric therapy system in which at least the therapy device (i.e., the implant) is designed to allow data transmission in at least two different data transmission modes, and the choice of a data transmission mode is made by a data communication control unit on the basis of at least one predefined selection criterion.

The data transmission modes preferably differ from each other with regard to at least one packet configuration of the transmitted data packets, and/or with regard to a protocol concerning the data transmission. The use of different protocols for a packet-oriented data transmission usually also implies different packet configurations. Switching between different data transmission modes is controlled automatically and preferably seamlessly by the data communication control unit, so that an existing data communication link is not terminated in switching and establishing of a new data communication link, but instead an existing data communication link is continued in another data transmission mode. This avoids requiring that a new connection be established in which the use parameters, including authentication information, must be exchanged between the therapy device and the external device. Such a process would take time, and may even require manual actions on the part of the user.

The data communication control unit is preferably designed to implement one of the available data communication modes on the basis of at least one of the following selection criteria:
- timeout of at least one timer (either in the therapy device or in the external device);
- detection of a user action, e.g., an input by a user (such as placement of a magnet near the implant);
- detection of a predefined device status, and/or
- detection of trouble.

The data communication control unit may operate according to fixedly predefined criteria, or it may be programmable. The data communication control unit is preferably designed so that
- any number of data transmission modes is or can be defined together with the respective packet configuration;
- the choice of a new data transmission mode may be made by the therapy device, the external device, or both;
- for selection of a data transmission mode:
  - timeouts are or can be defined such that they define the transition from a certain (or any) data transmission mode into another certain (or any) data transmission mode;
  - user actions are (or can be) defined such that they define the transition from a certain (or any) data transmission mode into another certain (or any) data transmission mode;
  - one or more operating states (device status) are (or can be) defined, detection of which prompts the data communication control unit to select a certain predefined or predefinable data transmission mode;
  - trouble cases are (or can be) defined, detection of which prompts the data communication control unit to select a predefined (or predefinable) data transmission mode;
  - it is (or can be) defined that the transceiver may be temporarily shut down as a function of a data transmission mode (e.g., the data transmission rate would be zero for a predefined period of time);
  - it is (or can be) defined that temporary programming is activated or deactivated by the data communication control unit as a function of a selected data transmission mode, or transitions between two data transmission modes.

As mentioned previously, the therapy device may also have two therapy device data communication interfaces which differ from one another, at least with regard to their technical structure. The data transmission modes to be selected can also differ from one another through the choice of one or more of the two therapy device data communication interfaces. One of the therapy device data communication interfaces is preferably designed to perform a data transmission by means of an alternating electric field, while the other therapy device data communication interface is preferably designed to perform a data transmission by means of an alternating magnetic field.

In a preferred version of the invention, the data communication control unit of the therapy device is designed to select exactly one of the available therapy device data communication interfaces and to shut down one or more others as part of the selection of a data transmission mode.

A therapy device data communication interface may have multiple interface components, each of which may assume different operating states—for example, on or off—such that the data transmission modes to be selected may be differentiated from one another by a respective operating state of one or more of the interface components.

The data communication interface is preferably designed in particular to transmit the most important portion of the transmitted data over the inductive therapy device data communication interface in the case of the presence of an inductive telemetry, i.e., in the case of the presence of a programming device capable of communicating with a corresponding therapy device data communication interface via an alternating magnetic field. At the same time, the data communication interface completely stops a data transmission via a second therapy device data communication interface operating on the basis of an alternating electric field, or otherwise uses it only for additional less critical data. Such especially important data to be transmitted over the inductive therapy device data communication interface may include programming data; the most important data from an intracardiac electrocardiogram obtained in the therapy device; transmission of an emergency program; or triggering of an emergency shock.

The data communication control unit making the selection of a data transmission mode need not necessarily be accommodated in the device (therapy device or external device) that first performs the switching of the data transmission mode. For example, it is possible for a user action to be performed on the external device and detected by an emergency data communication control unit of the external device. Next the external device data communication interface may transmit a corresponding control sequence to the therapy device data communication control unit, which then changes the data transmission mode. One or both of the data communication control units involved in a respective transmission link may also be designed to generate and to transmit indicator data over the respective data transmission link, indicating whether the next data frame is to be transmitted over an inductive data transmission link or a high-frequency data transmission link.

BRIEF DESCRIPTION OF THE DRAWINGS

The invention will now be explained in greater detail on the basis of an exemplary version with reference to the figures, in which.

DETAILED DESCRIPTION OF EXEMPLARY VERSIONS OF THE INVENTION

Figure 1:
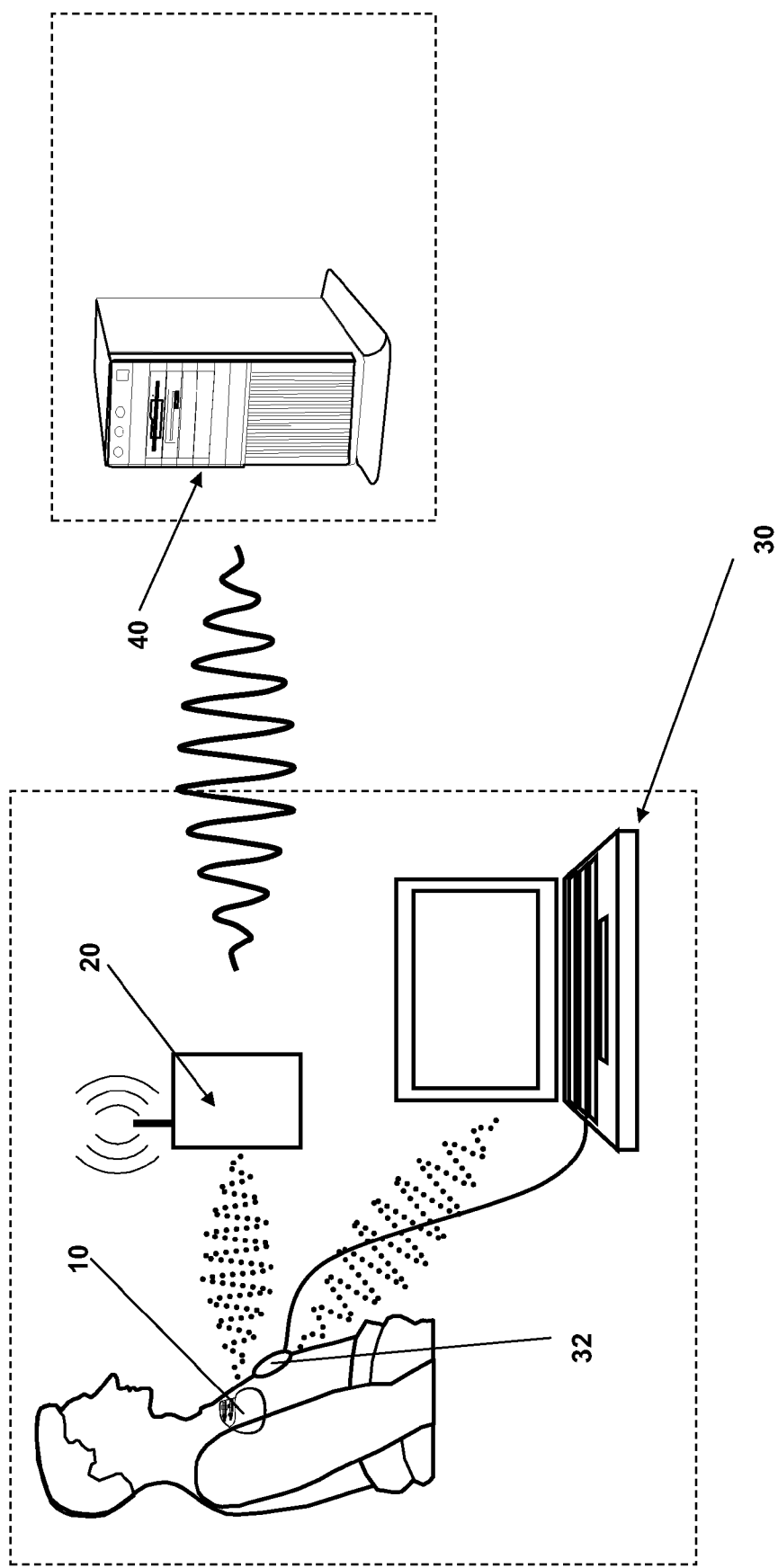
FIG. 1: shows an overview of an electric therapy system.

FIG. 1 shows a therapy device 10 in the form of an implantable heart pacemaker, a patient device 20 provided as a first external device, and a programming device 30 provided as a second external device. The programming device 30 has a programming head 32 allowing it to establish a short-range inductive telemetry application to the therapy device 10, in which data are transmitted wirelessly by means of an alternating magnetic field between the therapy device 10 and the programming head 32 of the programming device 30. To this end, both the therapy device 10 and the programming device 30 have a data communication interface for the inductive data transmission.

The therapy device 10 also has a second data communication interface for data transmission by means of high-frequency alternating electric fields, allowing it to transmit data wirelessly between the therapy device 10 and the patient device 20 or the programming device 30. The patient device 20 and the programming device 30 each have a corresponding data transmission interface. The patient device 20 also serves as a relay station for transmitting data between the therapy device 10 and a remote central service center 40.

Figure 2:
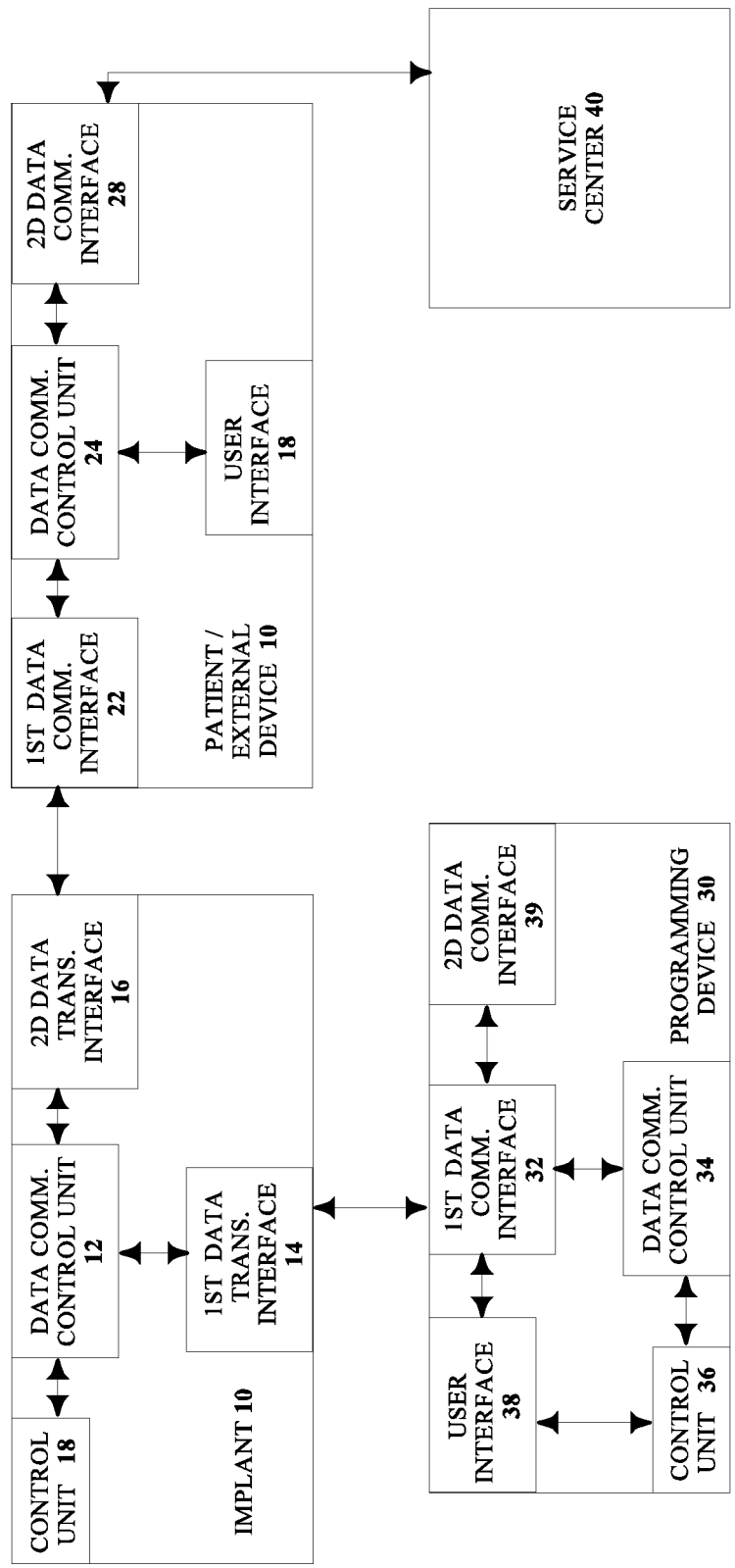
FIG. 2: shows a schematic block diagram of the components of the therapy system of FIG. 1.

FIG. 2 shows the individual components of the therapy system from FIG. 1 in a block diagram, where the components of the therapy system are shown schematically in simplified form. Typical components of a therapy device are not shown here, e.g., where the device is an implantable heart pacemaker, components such as connections for electrode lines, a stimulation generator, sensing units or a therapy control unit are not shown.

The therapy device 10 has a data communication control unit 12, which is connected to a first therapy device data transmission interface 14 and a second therapy device data communication interface 16. The first therapy device data communication interface 14 is designed as an inductive data communication interface for bidirectional transmission of data by means of alternating magnetic fields. The second therapy device data communication interface 16 is designed as a high-frequency data communication interface for bidirectional transmission of data by means of high-frequency alternating electric fields.

The first therapy device data communication interface 14 serves to allow communication with the programming device 30, while the second therapy device data communication interface 16 allows bidirectional data communication between the therapy device 10 and a patient device 20 or the programming device 30.

In addition, the therapy device 10 has a therapy device control unit 18, which is designed to control the operating states of the therapy device 10. The therapy device control unit 18 is connected to the therapy device data communication control unit 12 to allow transmission of data characterizing at least a few of the detected operating states.

The patient device 20 has a (first external) data communication interface 22, which is designed to perform a bidirectional wireless data exchange with the second therapy device data communication interface 16 by means of a high-frequency alternating electric field. The data communication interface 22 of the external device 20 is connected to a data communication control unit 24 which controls, for example, the data communication unit 22 with regard to the parameters of the protocol to be used for a packet-oriented bidirectional data transmission. Furthermore, the data communication control unit 24 is designed to respond to user input/actions, which may be performed by a user via a corresponding user interface 26 of the patient device 20. The user interface 26 is therefore connected to the data communication control unit 24 of the patient device 20.

Furthermore, the patient device 20 also has a second external device data communication interface 28 for bidirectional remote transmission of data to and from the central service center 40. This data transmission may take place wirelessly, e.g., via a mobile radio network or in a hard-wired system.

The programming device 30 has a programming device data communication interface 32 which is designed to perform a bidirectional data transmission with the inductive therapy device data communication interface 14 by means of an alternating magnetic field by inductive telemetry. The programming device data communication interface 32 is also connected to a corresponding programming device data communication control unit 34 which controls the data transmission mode to be used, in particular the protocol for packet-oriented and bidirectional data transmission. The programming device data communication control unit 34 is connected to a central programming device control unit 36, which is in turn connected to a user interface 38. The user interface 38 allows user input to be received for controlling the programming device 30, and also for controlling the data transmission between the programming device 30 and the therapy device 10.

With respect to inductive telemetry between the therapy device 10 and the programming device 30, the inductive first therapy device data communication interface 14 is designed to automatically detect the proximity of a programming head of the programming device 30, which includes the programming device data communication interface 32. Preferably, this detection of the proximity of a programming head 32 is an event which is taken into account by the therapy device data communication control unit 12 in the selection of a respective data transmission mode to be used. Additional events and rules which influence and control the performance of the therapy device data communication control unit 12 will now be explained in greater detail below on the basis of the flow charts in FIGS. 3 and 4.

As shown in FIG. 2 and as already indicated in FIG. 1, in a preferred version of the invention, the programming device 30 also has a second programming device data communication interface 39, which is designed for bidirectional data transmission between the second programming device data communication interface 39 and the second therapy device data communication interface 16 via a high-frequency (HF) alternating electric field. The programming device data communication control unit 34 may select the first programming device data communication interface 32, the second programming device data communication interface 39, or both as part of the selection of a data transmission mode.

Figure 3:
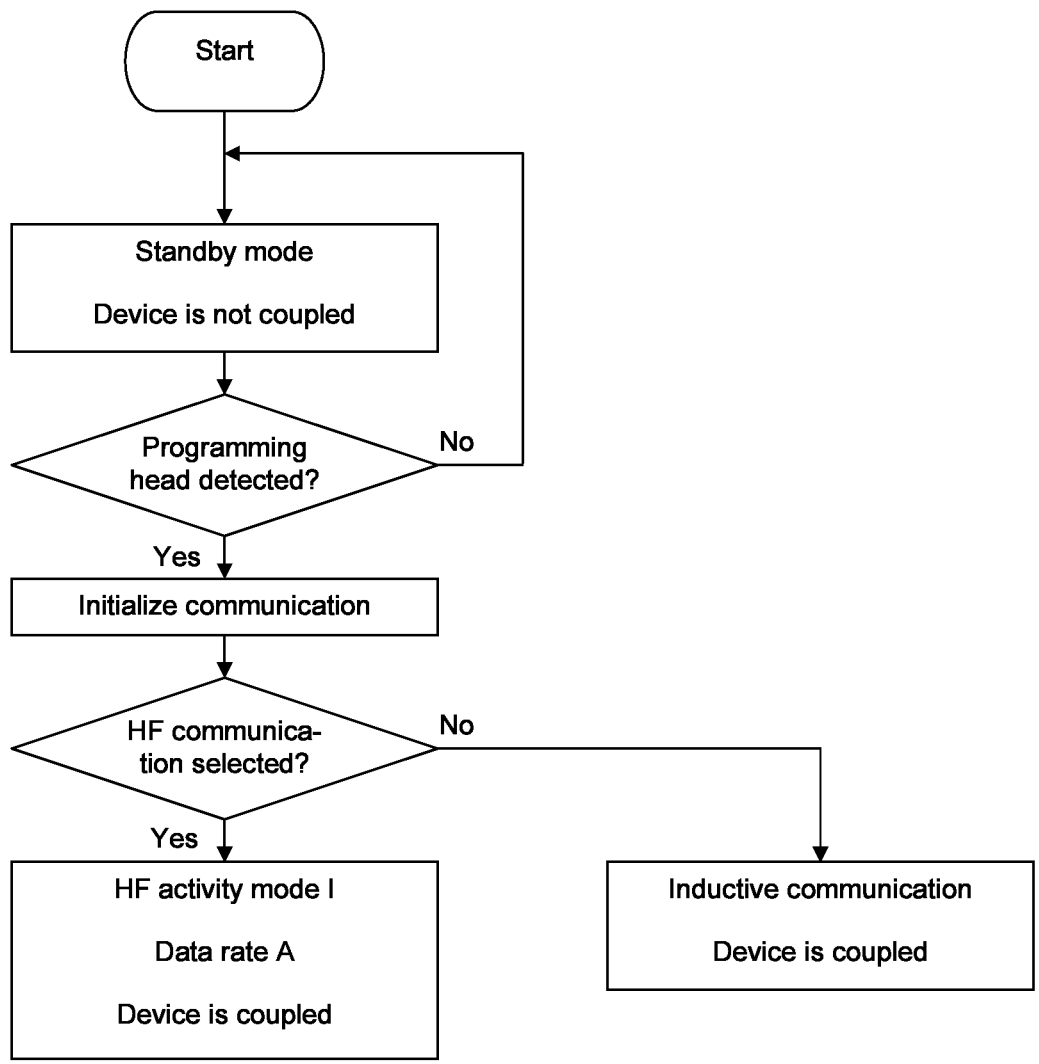
FIG. 3: shows a flow chart for initiating communication between a therapy device and an external device.
Figure 4:
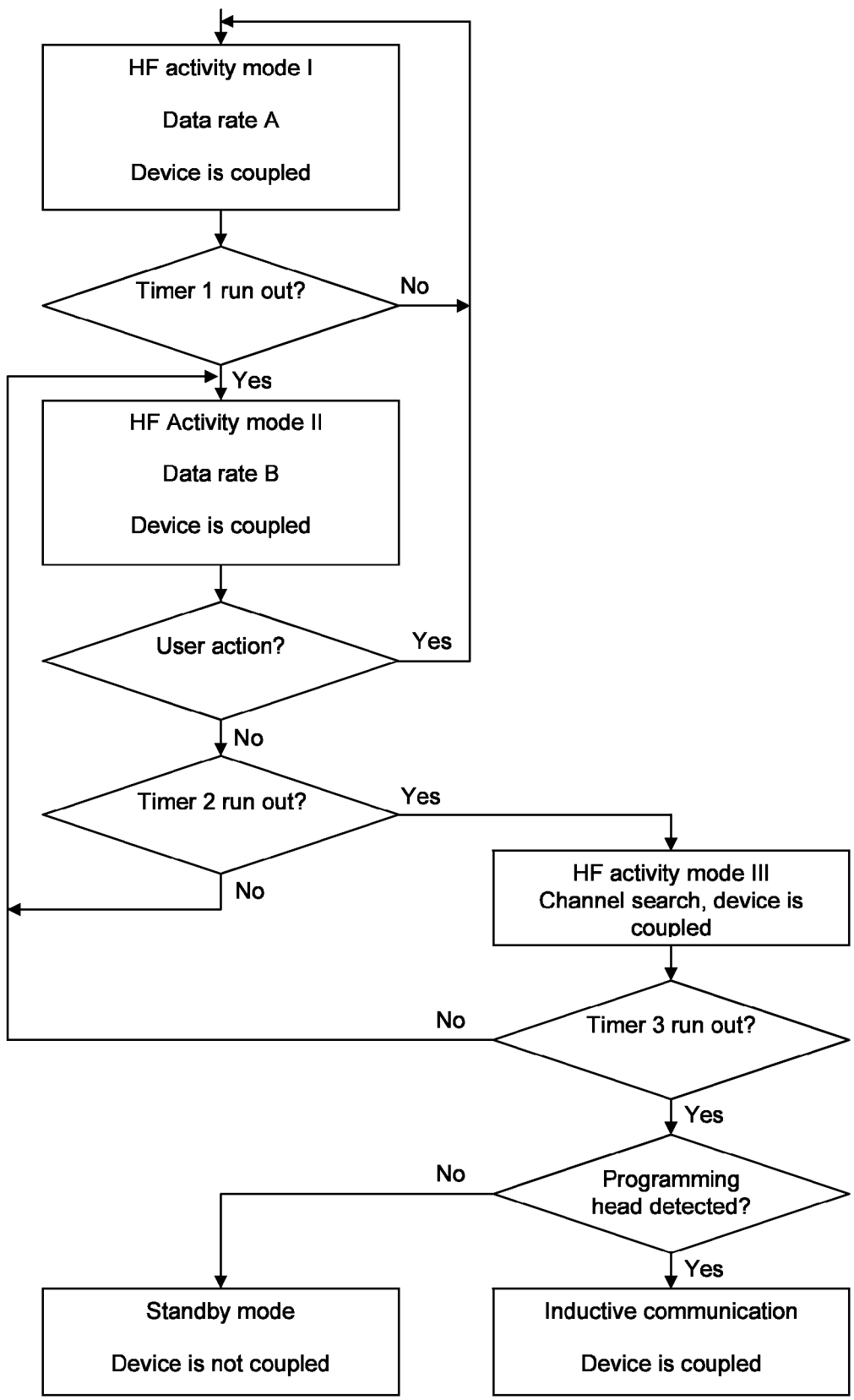
FIG. 4: is a continuation of the flow chart of FIG. 3 illustrating changing of the data transmission modes of the therapy device
Figure 5:
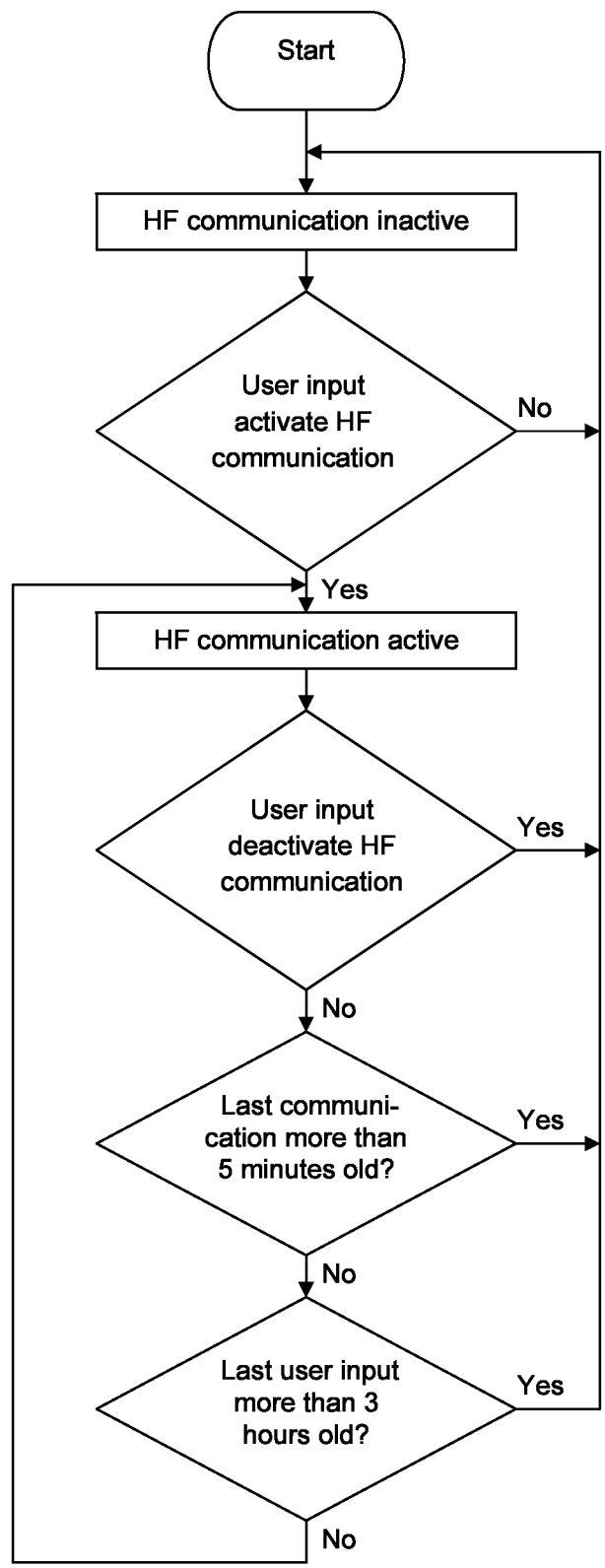
FIG. 5 shows a flow chart illustrating changing between different states of the programming device.

FIGS. 3 through 5 illustrate the state transitions between the individual HF data transmission modes. These are each labeled as HF activity mode in the figures. Ultimately they lead either to standby mode or to inductive communication. For reasons of simplicity, the flow chart does not show that inductive communication can be induced by positioning the programming head 32 (FIG. 2) adjacent the therapy device 10 (also FIG. 2) in HF activity mode 1 or 2 (seen in FIG. 4). This is possible by means of an additional query as to whether the programming head has been recognized after reception of a data packet.

FIGS. 3 and 4 relate to the data transmission modes of the therapy device 10 for data transmission over the second therapy device data communication interface 16 by means of a high-frequency alternating electric field. These data transmission modes I through III are labeled as HF activity modes I through III in FIGS. 3 and 4. A fourth data transmission mode is inductive communication between the therapy device 10 and the programming device 30. Thus, a total of four data transmission modes are provided for the therapy device 10, namely three HF activity modes I through III and one inductive communication mode. The change between individual data transmission modes of the therapy device 10 is controlled by its therapy device data communication control unit 12.

FIG. 3 shows how the therapy device 10 establishes a data transmission link with a programming device 30. Originally, the therapy device 10 is in an operating mode in which the therapy device 10 is not linked to any external device, i.e., specifically not to a programming device 30. This operating mode is known as standby mode. In this operating mode, the therapy device 10 asks regularly whether it detects the proximity of a programming head 32 via its inductive data communication interface 14. If this is not the case, the therapy device 10 remains in standby mode. For the case when the inductive data communication interface 14 detects a programming head 32, a data communication is initiated ("initialize communication" box in FIG. 3). As part of a data exchange during initiation of the data communication, the therapy device 10 checks on whether the data transmitted and received indicate that communication by means of a high-frequency alternating electric field is desired on the part of the programming device 30 ("HF communication selected?" diamond). If this is the case, the therapy device 10 activates the high-frequency second data communication interface 16 for bidirectional transmission of data. For this case, the therapy device 10 is designed to implement a first data transmission mode I (labeled as "HF activity mode I" in FIG. 3) in which data can be transmitted at the highest possible data rate A between the therapy device 10 and the programming device 30. The therapy device 10 is then in a state in which the therapy device 10 is linked to the programming device 30.

If the data received by the programming device 30 during initialization of data communication indicate that communication via a high-frequency alternating electric field is not desired, the therapy device 10 will initialize an inductive data transmission mode (inductive communication) by establishing wireless communication between the therapy device 10 and the programming device 30 over the respective inductive data communication interface 14/32. The therapy device data communication control unit 12 is thus designed so that it first activates the data transmission mode I (HF activity mode I) in response to being activated and does so by performing a data transmission using a protocol for packet-oriented data transmission that allows the highest possible data rate A.

Under some circumstances, the therapy device 10 automatically switches to a different data transmission mode which is associated (for example) with a lower data rate. This is illustrated in FIG. 4. The therapy device 10 is initially in the data transmission mode I having the highest data transmission rate. In this data transmission mode I, after initializing the data transmission, the therapy device 10 and the respective programming device 30 are coupled and bidirectional data transmission takes place therebetween. During such an active data link, the data communication control device 12 reacts in response to input by a user. Furthermore, a first timer (Timer 1) is constantly running during an active data link and is reset either when a user input is made or when the required data rate is higher than data rate B in the data transmission mode II. If there is no user input and/or if the required data rate is constantly lower than data rate B, then the first timer (Timer 1) runs for (preferably) five minutes and then ends with a timeout. In this case, the therapy device data communication control unit 12 initializes a change from the data transmission mode 1 to a data transmission mode 2 (HF activity mode 2): the data link between the therapy device 10 and the programming device 30 is still active, but a protocol for packet-oriented bidirectional data transmission is used that has a different packet configuration, resulting in a lower data rate B and requiring less energy than the data transmission in the data transmission mode I at data rate A.

If there is a user input (user action) during the HF activity mode II, the therapy device data communication control unit 12 initiates a change from the data transmission mode II back to the data transmission mode I. While the therapy device 10 is in this data transmission mode II, a second timer (Timer 2) is active, having a timeout after (preferably) one second and then always being reset when the data communication interface 16 of the therapy device receives a data packet. If the second data communication interface 16 of the therapy device 10 does not receive a data packet for one second, then there is a timeout of the second timer, with the result that the data communication control unit 12 of the therapy device 10 controls a change from the data transmission mode II to a data transmission mode III (HF activity mode III) in which the therapy device 10 and the respective programming device 30 are still linked together. In this data transmission mode III, the second data communication interface 16 of the therapy device 10 performs a channel search for any active (additional) data transmission channels. A third timer (Timer 3) is started at the same time; it has a timeout after (preferably) five minutes and is then reset when the channel search in the transmission mode III results in the second data communication interface 16 finding an active data transmission channel. Then the therapy device 10 returns to the data transmission mode II and uses the active data transmission channel thereby found for it.

If there is a timeout of the third timer (Timer 3) after five minutes, the therapy device 10 queries the first inductive data communication interface 14 and checks on whether this first data communication interface 14 has detected the proximity of a programming head 32. If this is the case, the therapy device 10 goes into the inductive data transmission mode in which the therapy device 10 and the programming device 30 are linked together by the two inductive data communication interfaces 14/32.

If the third timer (Timer 3) has run out after five minutes and then does not detect proximity of a programming head via the first data communication interface 14, then the therapy device 10 switches back to the standby mode in which it is not linked to a programming device 30. The second data communication interface 16 is then turned off and the data link is severed. The therapy device 10 and the programming device 30 are no longer linked together.

Additional details can be found in the flow charts in FIGS. 3 and 4. For sake of simplicity, the flow charts do not show that a transition to the inductive data communication mode can be forced at any time by positioning the programming head when in the data transmission mode I or II.

The flow chart in FIG. 5 shows the possible data transmission modes of the programming device 30 with respect to a data transmission by means of the second programming device data communication interface 39 via a high-frequency alternating electric field. As shown in FIG. 5, the programming device 30 recognizes two data transmission modes, namely a first data transmission mode in which the data transmission via a high-frequency alternating electric field is active and a second data transmission mode in which the data transmission via a high-frequency alternating electric field is inactive. A change between these two data transmission modes may take place through targeted activation and deactivation, i.e., an event to be input via the user interface 38 and to be processed by the programming device data communication interface 34. However, a transition from the active data transmission mode to the inactive data transmission mode of the programming device 30 may also take place in a timer-controlled manner. Thus the transition from the active data transmission mode to the inactive data transmission mode may take place either after a timeout of a first programming device timer when the programming device data communication control unit 34 receives no data packet on the part of the therapy device 10 for more than (for example) five minutes after transmitting the last data packet, or after the control unit 36 of the programming device 30 does not detect any user input for (for example) three hours after a timeout of a second programming device timer.

Figure 6:
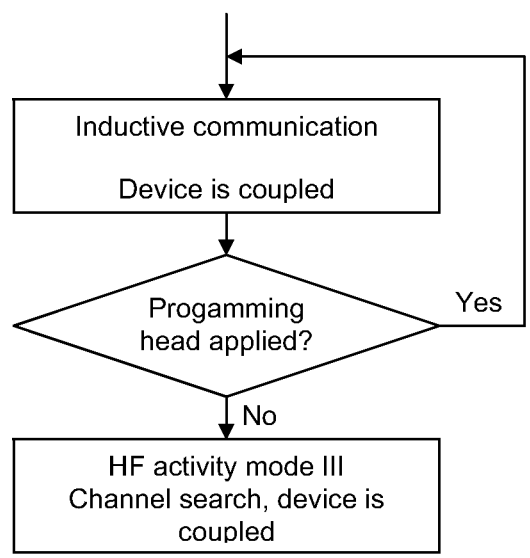
FIG. 6 shows the seamless transition from inductive communication back to HF communication.

Finally, FIG. 6 illustrates that a change between data transmission by means of high-frequency alternating electric field and inductive data transmission takes place seamlessly. As soon as the programming head 32 has been removed, the therapy device 10 automatically returns to the data transmission mode III (HF activity mode III).

In summary, this yields a therapy device having at least one data communication interface which can operate in various data transmission modes and cooperate with a data communication control unit, such that the data communication interface can change in a controlled manner from one data transmission mode to another in a process that is controlled by the data communication control unit as a function of predefined selection criteria without any interruption of an existing data link.

Preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. An electric therapy system including a therapy device (10) having:
   a. a therapy device data communication interface (14, 16) configured to perform a wireless bidirectional data transmission establishing a data link, the therapy device data communication interface (14, 16) including:
      (1) an inductive data communication interface (14) configured to establish the data link wherein a wireless bidirectional data transmission of data packets occurs in an inductive data transmission mode via an alternating magnetic field, and
      (2) an electric data communication interface (16) configured to establish the data link wherein a wireless bidirectional data transmission of data packets occurs in an electric data transmission mode via an alternating electric field,
   the data packets containing one or more of:
      i. programming for the therapy device, and
      ii. patient data collected by the therapy device;

b. a therapy device data communication control unit (12) configured to:
  (1) control the therapy device data communication interface (14, 16) so that the data transmission by the therapy device data communication interface (14, 16) takes place in one of the data transmission modes;
  (2) select one of the data transmission modes for use, the selection being based on one or more predefined selection criteria, and
  (3) change from one of the data transmission modes to another of the data transmission modes during the data link:
    (a) after transmission of some of the data packets, and
    (b) upon occurrence of an event corresponding to one of the selection criteria,
    so that the data link is not interrupted, and rather is continued in another of the data transmission modes.

2. The electric therapy system of claim 1 wherein the data transmission modes differ from one another with regard to one or more of:
  a. a packet configuration for the data transmission, and
  b. a protocol for the data transmission.

3. The electric therapy system of claim 1 wherein the predefined selection criteria include one or more of:
  a. timeout of at least one timer,
  b. user-activated input,
  c. status of the therapy device (10), and/or
  d. detection of a disturbance.

4. The therapy device of claim 1 wherein the therapy device data communication control unit (12) is further configured to:
  a. respond to control signals received over the therapy device data communication interface (14, 16), and
  b. select one of the data transmission modes for use as a function of a received control signal.

5. The therapy device of claim 1 wherein:
  a. the therapy device (10) is configured to detect the proximity of a programming head (32) emitting an alternating magnetic field, and
  b. the therapy device data communication control unit (12) is configured to select one of the data transmission modes in dependence on whether the programming head (32) is in proximity to the therapy device (10).

6. The electric therapy system of claim 1 wherein the therapy device data communication control unit (12) is configured to control the therapy device data communication interface (14, 16) to perform the data transmission with the external device (20, 30):
  a. ordinarily in the electric data transmission mode via the electric data communication interface (16), and
  b. otherwise in the inductive data transmission mode via the inductive data communication interface (14) when the inductive data communication interface (14) detects an alternating magnetic field emitted by a programming head (32) of the external device (20, 30).

7. The electric therapy system of claim 1 wherein the therapy device data communication control unit (12) is configured to control the therapy device data communication interface (14, 16) to perform the data transmission with the external device (20, 30):
  a. in the inductive data transmission mode via the inductive data communication interface (14) when the inductive data communication interface (14) detects an alternating magnetic field emitted by a programming head (32) of the external device (20, 30);
  b. in the electric data transmission mode via the electric data communication interface (16) when the inductive data communication interface (14) receives an instruction from the external device (20, 30), while in the inductive data transmission mode, that data transmission via an alternating electric field is desired.

8. The electric therapy system of claim 7 wherein the electric data transmission mode:
  a. has a data transmission rate which is decreased, and/or
  b. has a data transmission channel which is changed,
  when data transmission with the external device (20, 30) is unsuccessful.

9. The electric therapy system of claim 7 wherein the electric data transmission mode:
  a. attempts to perform the data transmission with the external device (20, 30) at a first data transmission rate; and
  b. attempts to perform the data transmission with the external device (20, 30) at a second data transmission rate lower than the first data transmission rate, when the data transmission at the first data transmission rate is unsuccessful.

10. The electric therapy system of claim 9 wherein the electric data communication interface (16) attempts to locate a channel allowing performance of the data transmission with the external device (20, 30) when the data transmission at the second data transmission rate is unsuccessful.

11. The electric therapy system of claim 1 wherein the data communication control unit (12) of the therapy device (10) is configured to:
  (1) a. select one of the two data communication interfaces (14, 16), and
  (2) b. turn off the other when the one is selected.

12. The electric therapy system of claim 1 wherein the therapy device data communication control unit (12), when selecting one of the data transmission modes, selects:
  (1) a. one of the data communication interfaces (14, 16), or
  (2) b. both of the data communication interfaces (14, 16).

13. The electric therapy system of claim 1 wherein:
  a. at least one of the data communication interfaces (14, 16) has multiple interface components, each of which may assume different operating states, and
  b. different ones of the data transmission modes use different ones of the operating states of the interface components.

14. The electric therapy system of claim 13 wherein the operating states include:
  a. a deactivated state, and
  b. one or more activated states.

15. The electric therapy system of claim 1 further including an external device (20, 30) having:
  a. an external device data communication interface (22, 32, 39) configured to perform a bidirectional wireless data transmission establishing the data link with the therapy device data communication interface (14, 16), and
  b. an external device data communication control unit (24, 34) configured to control the external device data communication interface (22, 32, 39) so that the data transmission by the external device data communication interface (22, 32, 39) takes place in a chosen one of the different data transmission modes.

16. An electric therapy system including
  I. a therapy device (10) having:
    A. a therapy device data communication interface (14, 16) configured to perform a wireless bidirectional data transmission establishing a data link, and
    B. a therapy device data communication control unit (12) configured to control the therapy device data communication interface (14, 16), II. an external device (20, 30) having:
  A. an external device data communication interface (22, 32, 39) configured to establish the data link wherein a wireless bidirectional data transmission of data packets occurs, the data packets containing one or more of:
    i. programming for the therapy device, and
    ii. patient data collected by the therapy device;
  B. an external device data communication control unit (34) configured to control the external device data communication interface (22, 32, 39),
wherein:
a. the data communication control units (12, 34) control the data communication interfaces (14; 16; 22; 32; 39) so that the data transmission takes place in one of:
  (1) an inductive data transmission mode utilizing an alternating magnetic field, and
  (2) an electric data transmission mode utilizing an alternating electric field,
b. at least one of the two data communication control units (12, 34) is configured to
  (1) select one of the data transmission modes for use, the selection being based on:
    i. one or more predefined selection criteria, and
    ii. on occurrence of an event corresponding to one of the selection criteria,
  (2) change from one of the data transmission modes to another of the data transmission modes
    i. during the data link, and
    ii. after transmission of some of the data packets,
    so that the data link is not interrupted, and rather is continued in another of the data transmission modes.

17. The electric therapy system of claim 16 wherein the data transmission modes differ from one another with regard to one or more of:
  a. the packet configuration, and
  b. the protocol,
  for the data transmission.

18. The electric therapy system of claim 16 wherein the predefined selection criteria include one or more of:
  a. timeout of at least one timer,
  b. user-activated input,
  c. status of the therapy device (10), and/or
  d. detection of a disturbance.

19. The electric therapy system of claim 16 wherein:
  a. the therapy device (10) has two data communication interfaces (14, 16) which differ from one another; and
  b. different ones of the data transmission modes use different ones of the data communication interfaces (14, 16).

20. The electric therapy system of claim 19 wherein the data communication control unit (12) of the therapy device (10) is configured to:
  a. select one of the two data communication interfaces (14, 16), and
  b. turn off the other when the one is selected.

21. The electric therapy system of claim 16 wherein:
  a. at least one of the data communication interfaces (14, 16) has multiple interface components, each of which may assume different operating states, and
  b. different ones of the data transmission modes use different ones of the operating states of the interface components.

22. The electric therapy system of claim 21 wherein the operating states include:
  a. a deactivated state, and
  b. one or more activated states.

* * * * *